United States Patent [19]
Dennison, Jr.

[11] Patent Number: 5,036,309
[45] Date of Patent: Jul. 30, 1991

[54] PORTABLE SYSTEM AND METHOD FOR CONTINUOUSLY MONITORING PROTECTIVE CLOTHING FOR DETECTING AND SIGNALING THE OCCURRENCE OF A BREACH THEREIN

[76] Inventor: Everett G. Dennison, Jr., 200 Glenview Rd., Canfield, Ohio 44406

[21] Appl. No.: 537,811

[22] Filed: Jun. 14, 1990

[51] Int. Cl.⁵ .............................................. G08B 21/00
[52] U.S. Cl. ...................................... 340/540; 128/897; 128/898; 128/917; 128/918; 340/605; 606/34
[58] Field of Search ............... 340/540, 647, 604, 605; 606/34; 128/897, 898, 917, 918

[56] References Cited
U.S. PATENT DOCUMENTS
4,956,635  9/1990  Langdon ............................. 340/540

Primary Examiner—Glen R. Swann, III
Attorney, Agent, or Firm—Terry M. Gernstein

[57] ABSTRACT

A portable unit is releasably attachable to a worker, and an electrical network that has fully insulated wires releasably connected to the worker and a workpiece to the portable unit. The unit includes an amplifier and a sensitivity-adjusting element so that breaches in the worker's protective clothing as small as one molecule can be large enough to cause activation of an alarm.

27 Claims, 3 Drawing Sheets

PORTABLE SYSTEM AND METHOD FOR CONTINUOUSLY MONITORING PROTECTIVE CLOTHING FOR DETECTING AND SIGNALING THE OCCURRENCE OF A BREACH THEREIN

TECHNICAL FIELD OF THE INVENTION

The present invention relates to the general art of wearing apparel, and to the particular field of protective clothing.

BACKGROUND OF THE INVENTION

In many industries, a worker may not want any portion of a workpiece to contact any portion of his or her skin. This situation occurs in the chemical industry as well as in several other industries. For this reason, the art contains various examples of protective apparel, such as gloves, aprons, boots, pants, smocks, face shields, gowns and the like.

As more is known of various communicable diseases, more and more workers are using such protective garments in their work. Thus, it is not uncommon to find beauticians or other such workers wearing certain types of protective wearing apparel.

The most notable examples of the use of protective clothing are in the medical field. Thus, nearly all doctors wear some sort of protective apparel when working on a patient. It is not uncommon for even dentists to wear protective gloves, masks, gowns, smocks and pants while performing routine examinations and dental procedures. The use of such protection is not limited to doctors, for technicians, nurses, emergency personnel, dental hygienists, and veterinarians are but a few examples of those in the medical field who now commonly wear some sort of protective clothing while carrying out their work. This list is merely representative of the many workers who will benefit from the use of protective clothing, and many other types of workers will occur to those skilled in the art based on the teachings of this disclosure.

Of course, anyone involved in any way with laboratory work in many fields, especially the medical field, almost always wears some sort of protective clothing.

The surgeon and other operating room and hospital personnel are the most visible examples of medical personnel who wear protective clothing while working. Not only do such personnel wear protective clothing to protect a patient from contamination, with the advent of diseases such as hepatitis, AIDS and the like, many such medical workers wear protective clothing to protect themselves from contamination.

While the integrity of all such protective garments must be ensured, the surgical glove has received much attention in the art. One study has found that as much as fifty-nine percent of tested surgical gloves developed leaks when tested every fifteen minutes during surgery, and leakage occurred twenty-five percent of the time when two pairs of gloves were worn. This leakage is probably even higher for certain operations, such as in orthopaedic surgery, or the like. Any leakage of the surgical gloves can prove to be dangerous, and should be determined on a regular basis so the medical personnel can be warned upon the occurrence of such a breach.

Therefore, the art has included various procedures which are intended to protect the integrity of a worker's gloves, especially surgical gloves. These procedures have included requirements for a worker to change his gloves at a regular interval, or which require a worker to wear several pairs of gloves. Such procedures are not entirely successful because they interrupt the worker from his work and break his concentration. Furthermore, wearing several pairs of gloves may interfere with proper performance of the task. Even then, as the above-mentioned study found, the worker may not be fully protected.

Thus, the art has also included devices and systems which are intended to detect breaches in a worker's gloves. One such device requires the worker to immerse his gloved hands in a vat of electrolyte. However, this device also requires the worker to interrupt his task, move his hands to the vat, and immerse them in the electrolyte. Perhaps, the worker will have to wash his hands thoroughly before using this device to avoid contaminating the vat or the electrolyte, especially if the task may involve a contagious disease. This could be a clumsy and distracting requirement especially for a surgeon where time can be of the essence. Furthermore, the protection occurs only when the worker stops his task and tests the gloves. Breaches in the gloves may have occurred some time before the test, and thus exposed the worker to contamination during the time between the occurrence of the breach and the test. Due to the need to interrupt the work, many surgeons will simply delay testing their gloves until a convenient stopping place during the surgery has arisen thereby possibly increasing the risk of exposure. This is a problem in procedures requiring the surgeon to change gloves as well.

The device disclosed in U.S. Pat. No. 4,321,925 is intended to continuously monitor a surgeon's gloves to warn of any perforations in those gloves. This device includes a contact on the patient, a contact on the surgeon, and an electrical path through the doctor's shoe, and through the operating room floor to and through the base of the operating table and to and through the table.

While this device overcomes some of the above-mentioned problems, it still has several drawbacks.

One drawback occurs because the electrical network which includes the signal means, the contacts, and the power source is not insulated for a portion thereof. Such uninsulated portion of the network includes the operating room floor, the operating table and the table base. Because of this, the characteristics of the circuit are not entirely and accurately predictable and may not be repeatable. For example, if there is a table base floor bolt that accidentally makes electrical contact with some other portion of the floor or room, the overall characteristics of the circuit can be changed enough so that the device which may have been sensitive enough to detect small leaks in the gloves during a particular operation will no longer be sensitive enough to detect such leaks. This situation may also occur if the doctor accidentally steps on some sort of insulating material and thus partially or totally insulates the bottom portion of the shoe heel that is intended to make contact with the floor. The device should therefore be calibrated before each operation, and even during the performance of a single operation to be sure that the desired sensitivity has not changed due to the occurrence of some event outside, or even inside, the operation.

Furthermore, this device is not adaptable to use in areas or environments outside of the specific operating room for which it was designed and calibrated. Thus, if an operation is to be performed on a gurney, or in the patient's bed, or even in a hallway or outside the hospital, such device may not operate in the manner intended. This is especially so in the case of ambulance personnel where operations are routinely carried out using supports that do not include an electrically conductive table which is connected to an electrically conductive floor by an electrically conductive base, all having electrical characteristics that are accounted for in a previously-conducted calibration procedure.

Still further, the patented device requires a specially designed shoe having a special heel. Many surgeons, or other medical personnel, may not wear such heeled shoes.

Still further, the patented device may be costly for several reasons. First, the operating room must be specially designed or retrofitted to use the device. Second, in may cases, once an item of clothing becomes contaminated, it is discarded. Should the special shoes of the patented device become contaminated, they may have to be replaced. Still further expense may be added if one of the elements of the network becomes contaminated, and must be replaced. Such replacement may require the entire network to be dismantled which can be time consuming as well as expensive. Spare parts may be difficult and costly to keep on hand, which is a drawback in an ambulance situation.

Still further, the patented device requires an electrically conductive floor which may not be desirable in some situations as some such floors may become slippery or may be uncomfortable.

Due to the requirement of a special shoe, the doctor may be required to change shoes before beginning a procedure. This may not be desirable, especially in an emergency situation.

While ensuring the integrity of a worker's gloves is quite important, due to the highly contagious and dangerous nature of many diseases and many chemicals, integrity monitoring of a worker's gloves alone may not be sufficient protection. In many situations, including a surgical operating room, any physical contact with the workpiece may prove to be dangerous.

Therefore, even beyond the drawbacks and problems mentioned for the known glove testers per se, they may have shortcomings in that they do not monitor all of the protective clothing being worn by a worker. Should that worker have a breach in is or her face mask, for example, such breach can be dangerous if the worker must bring his or her face in close proximity to a patient, for example to perform the work, as might be the case of an ambulance worker who must find and grasp a patient's tongue to prevent choking.

Therefore, there is a need for a system for continuously monitoring protective clothing to detect any breach in such clothing immediately upon occurrence of such breach, and which can be used to monitor all of the protective clothing worn by a worker, and which is adaptable to a wide variety of situations and environments, does not require the worker to stop work to check the integrity of the clothing, yet which provides repeatable, accurate results and which is easily transported and stored, and which is easily adjusted, donned and is still inexpensive.

OBJECTS OF THE INVENTION

It is a main object of the present invention to provide a system for continuously monitoring protective clothing to detect any breach in such clothing immediately upon occurrence of such breach.

It is another object of the present invention to provide a system for continuously monitoring protective clothing to detect any breach in such clothing immediately upon occurrence of such breach, and which can be used to monitor all of the protective clothing worn by a worker.

It is another object of the present invention to provide a system for continuously monitoring protective clothing to detect any breach in such clothing immediately upon occurrence of such breach, and which can be used to monitor all of the protective clothing worn by a worker, and which is adaptable to a wide variety of situations and environments.

It is another object of the present invention to provide a system for continuously monitoring protective clothing to detect any breach in such clothing immediately upon occurrence of such breach, and which can be used to monitor all of the protective clothing worn by a worker, and which is adaptable to a wide variety of situations and environments, does not require the worker to stop work to check the integrity of the clothing.

It is another object of the present invention to provide a system for continuously monitoring protective clothing to detect any breach in such clothing immediately upon occurrence of such breach, and which can be used to monitor all of the protective clothing worn by a worker, and which is adaptable to a wide variety of situations and environments, does not require the worker to stop work to check the integrity of the clothing, yet which provides repeatable, accurate results.

It is another object of the present invention to provide a system for continuously monitoring protective clothing to detect any breach in such clothing immediately upon occurrence of such breach, and which can be used to monitor all of the protective clothing worn by a worker, and which is adaptable to a wide variety of situations and environments, does not require the worker to stop work to check the integrity of the clothing, yet which provides repeatable, accurate results and which is easily transported and stored.

It is another object of the present invention to provide a system for continuously monitoring protective clothing to detect any breach in such clothing immediately upon occurrence of such breach, and which can be used to monitor all of the protective clothing worn by a worker, and which is adaptable to a wide variety of situations and environments, does not require the worker to stop work to check the integrity of the clothing, yet which provides repeatable, accurate results and which is easily transported and stored, and which is easily adjusted.

It is another object of the present invention to provide a system for continuously monitoring protective clothing to detect any breach in such clothing immediately upon occurrence of such breach, and which can be used to monitor all of the protective clothing worn by a worker, and which is adaptable to a wide variety of situations and environments, does not require the worker to stop work to check the integrity of the clothing, yet which provides repeatable, accurate results and which is easily transported and stored, and which is easily adjusted, donned and is still inexpensive.

SUMMARY OF THE INVENTION

These, and other, objects are achieved by a portable system and method for continuously monitoring protective clothing and which includes contacts which are placed on both a worker and on the workpiece and which are connected by a network that is fully insulated between the contacts. The network includes a portable unit that can be releasably attached to the worker and which has an amplifier and a sensitivity-adjusting element therein. Alarm devices are also mounted on the worker-attachable portable unit.

The amplifier includes an NPN transistor and has a gain of approximately 25000. The sensitivity-adjusting element includes a rheostat-type device, and the signal element includes audible and/or visual elements.

The electrical leads connecting the contacts to the portable unit are fully insulated and thus the overall network is not subject to outside influences which may alter or affect the sensitivity, accuracy or repeatability of the overall device.

Due to the fully insulated and portable nature of the device, it can be used in a wide variety of situations and environments to continuously monitor a large variety of different protective garments for a variety of different workers. The device is easily transported and stored, yet is quickly and easily donned by a worker and thus is not likely to interfere with a work procedure, especially in an emergency situation.

The device can be used to monitor any protective clothing worn by a worker in any environment or situation and can do so in a continuous, accurate and repeatable manner. The portable unit can be encased in a special container and can be worn by the worker in a location that is not likely to expose that portable unit to contact with the workpiece or any portion thereof, while the remaining elements of the network are releasably connected to that portable unit. The remaining elements of the network, including the insulated wires and the contacts, are relatively inexpensive and thus can be discarded and replaced if exposed to contact with the workpiece. If one of these elements is damaged or contaminated, it is easily and quickly replaced. Thus, for example, in an operating room, if fluids from a patient contact the insulated wires of the device, these wires can simply be discarded after the operation is completed and new wires used without incurring undue expense or time. In an ambulance, spare wires and contacts can be carried in case of damage.

BRIEF DESCRIPTION OF THE DRAWING FIGURES

DETAILED DESCRIPTION OF THE PREFERRED EMBODIMENT OF THE INVENTION

Figure 1:
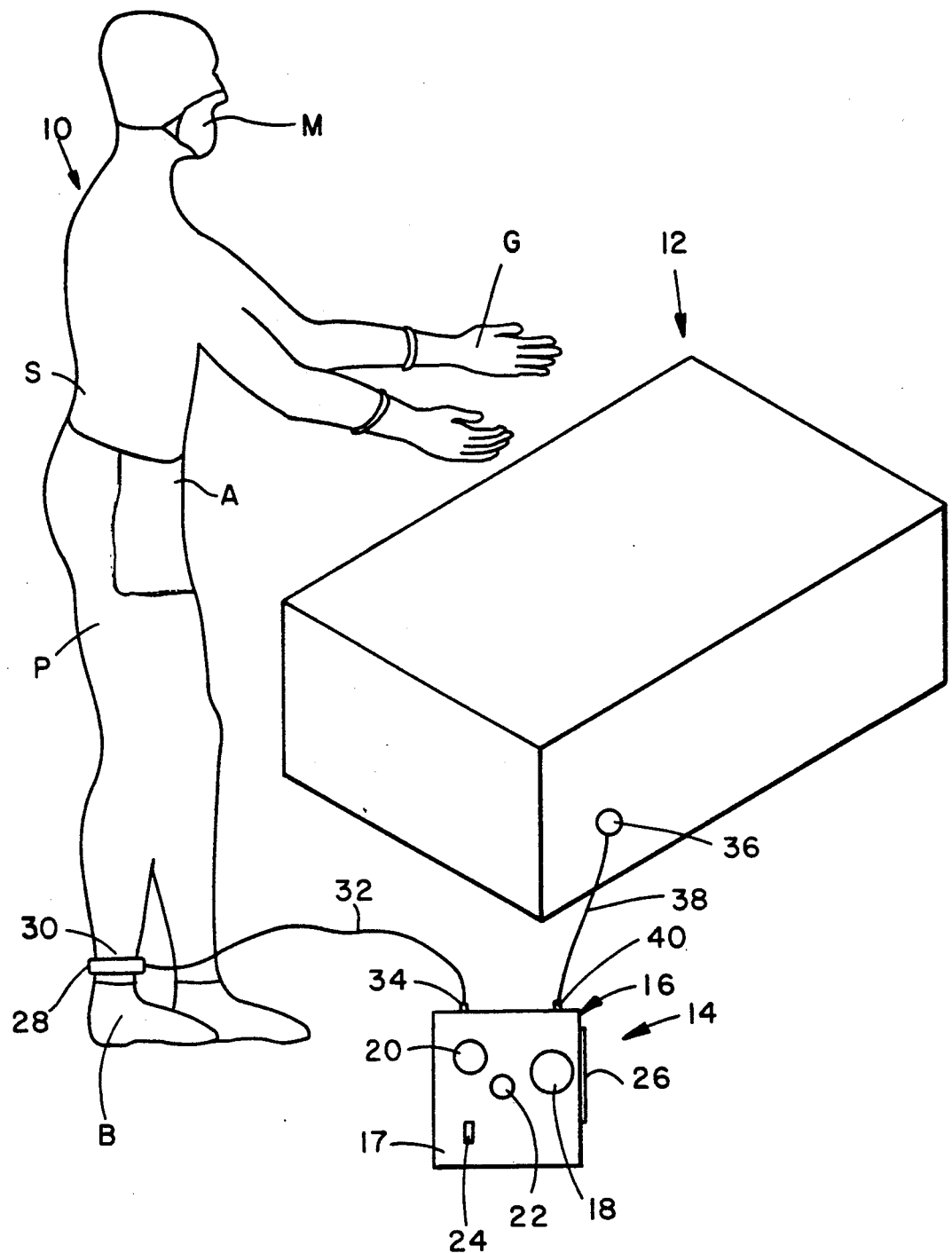
FIG. 1 illustrates the device of the present invention being connected to a worker and to a workpiece.

Shown in FIG. 1 is a worker 10 carrying out a procedure on a workpiece 12. The workpiece 12 is shown in general block form as it can be an inanimate object, such as a chemical or biological experiment, a quality control operation, or the like, as well as an animate object such as a human or an animal. Various applications will occur to those skilled in the art based on the teaching of the present disclosure, and thus the specific examples provided herein are not intended to be limiting, but only examples.

A system 14 is shown in FIG. 1 for electrically connecting the worker 10 to the workpiece 12, and embodies the present invention. The system 14 includes a portable unit 16 having a housing 17 which contains a power source (not shown in FIG. 1), and various circuit elements connecting that power source to an audible alarm element 18 and/or to a visible alarm element 20 via a sensitivity-adjusting element 22 and an on/off switch 24. A spring-type clip 26 is mounted on the housing to releasably attach the portable unit to the worker as in his pocket, on his belt or the like.

A first electrical contact element 28 is electrically attached to the worker in a location that will not interfere with his work, as on his ankle 30, or the like, and is connected to the circuit in the portable unit by a first fully insulated wire 32 that is releasably connected to that circuit via a jack-like connection 34. A second electrical contact element 36 is electrically connected to the workpiece and is connected to the circuit elements in the portable unit by a second fully insulated electrical wire 38. The second wire is releasably connected to that circuit via a jack-like connection 40.

The worker 10 is shown wearing various items of protective clothing, such as gloves, such as a surgical glove G, boots, such as boot B, a smock or gown S, pants P, an apron A, a face covering such as mask M or the like. As will be apparent from the ensuing discussion, the protective clothing worn by the worker is electrically insulating, and prevents electrical contact between the worker and the workpiece and, hence, the contact 36. However, should any part of the worker contact any portion of the workpiece in a manner that completes the electrical circuit as via a breach in that protective clothing, there will be electrical contact between the contact elements 28 and 36 thereby completing the circuit and activating the alarm element or elements.

Figure 2:
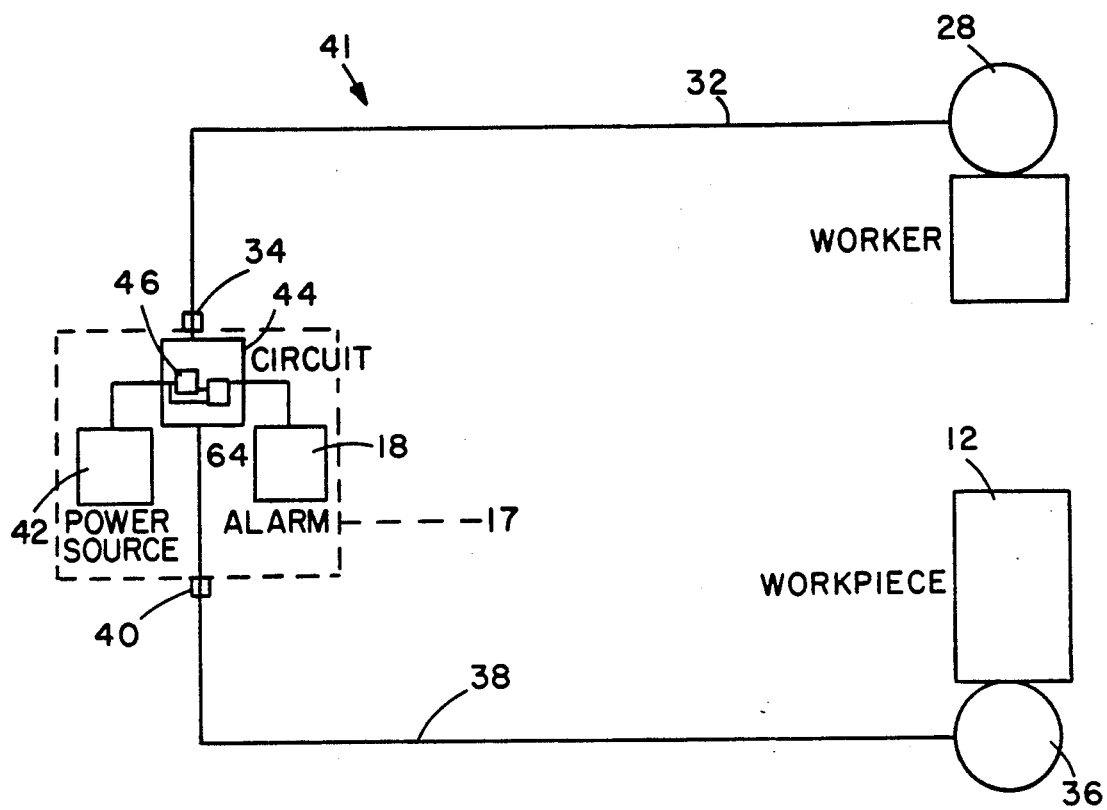
FIG. 2 is a block diagram of the overall system embodied in the device of the present invention.

FIG. 2 illustrates the overall network 41 in block diagram form, and shows a power source 42 connected to circuit 44. The jack-type connections 34 and 40 as well as the wires 32 and 38 and the contact elements 28 and 36 are all fully electrically insulated to prevent the overall electrical characteristics of the network 41 from being altered by the influence of outside forces, such as accidental contact with electrically conductive elements or contact with materials that may change their electrical characteristics.

Figure 3:
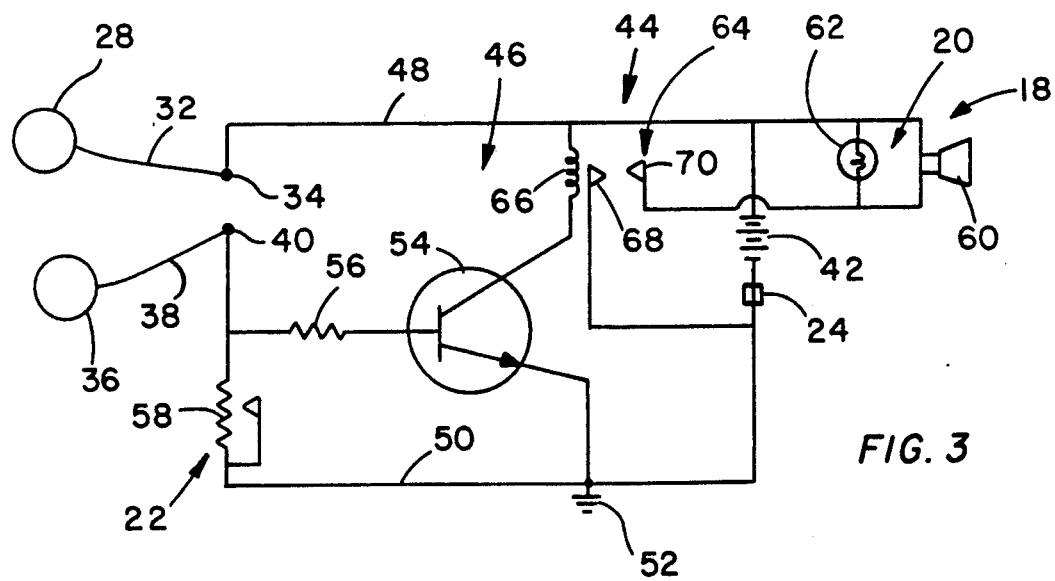
FIG. 3 is a circuit diagram of the device of the present invention.

The circuit 44 is shown in FIG. 3 as including an amplifier device 46 connected to the power source by line conductors 48 and 50 as well as to ground 52. The preferred form of the amplifier includes an NPN transistor 54 and has a gain of approximately 25000. A resistor 56 is also included in the circuit. The sensitivity-adjusting element 22 includes a rheostat-type device 58, and the alarm element includes a horn 60 as well as a light 62 both electrically connected to the amplifier by a relay-type switch 64 that is controlled by the amplifier 46.

As can be seen from FIG. 3, the contacts 28 and 36 are electrically spaced apart from each other. In such condition, the switch 64 is open and no power is supplied from source 42 to the alarm elements. However, electrically connecting contacts 28 and 36 completes the amplifier circuit, and the amplifier activates coil 66 to cause switch contact 68 to electrically contact switch contact 70 thereby completing an electrical path between the alarm elements and the power source to activate such alarm elements.

Figure 5:
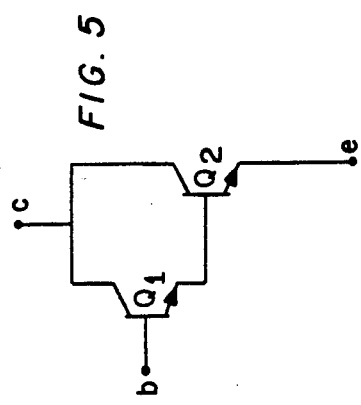
FIG. 5 illustrates a Darlington configuration.

The sensitivity of the circuit can be adjusted by the rheostat element 58 so that the alarm elements will be activated according to the desired amount of current flowing between contacts 28 and 36. The power source can be a nine volt battery or less as suitable. The on/off switch 24 is shown adjacent to the power source, but could be included in any suitable location in the circuit. An alternative form of the amplifier could include a Darlington pair as disclosed in standard textbooks such as "Microelectronic Circuits" by Adel S. Sedra and Kenneth C. Smith, published by Holt, Rinehart and Winston in 1982 (see page 509), and as shown herein in FIG. 5.

Figure 4:
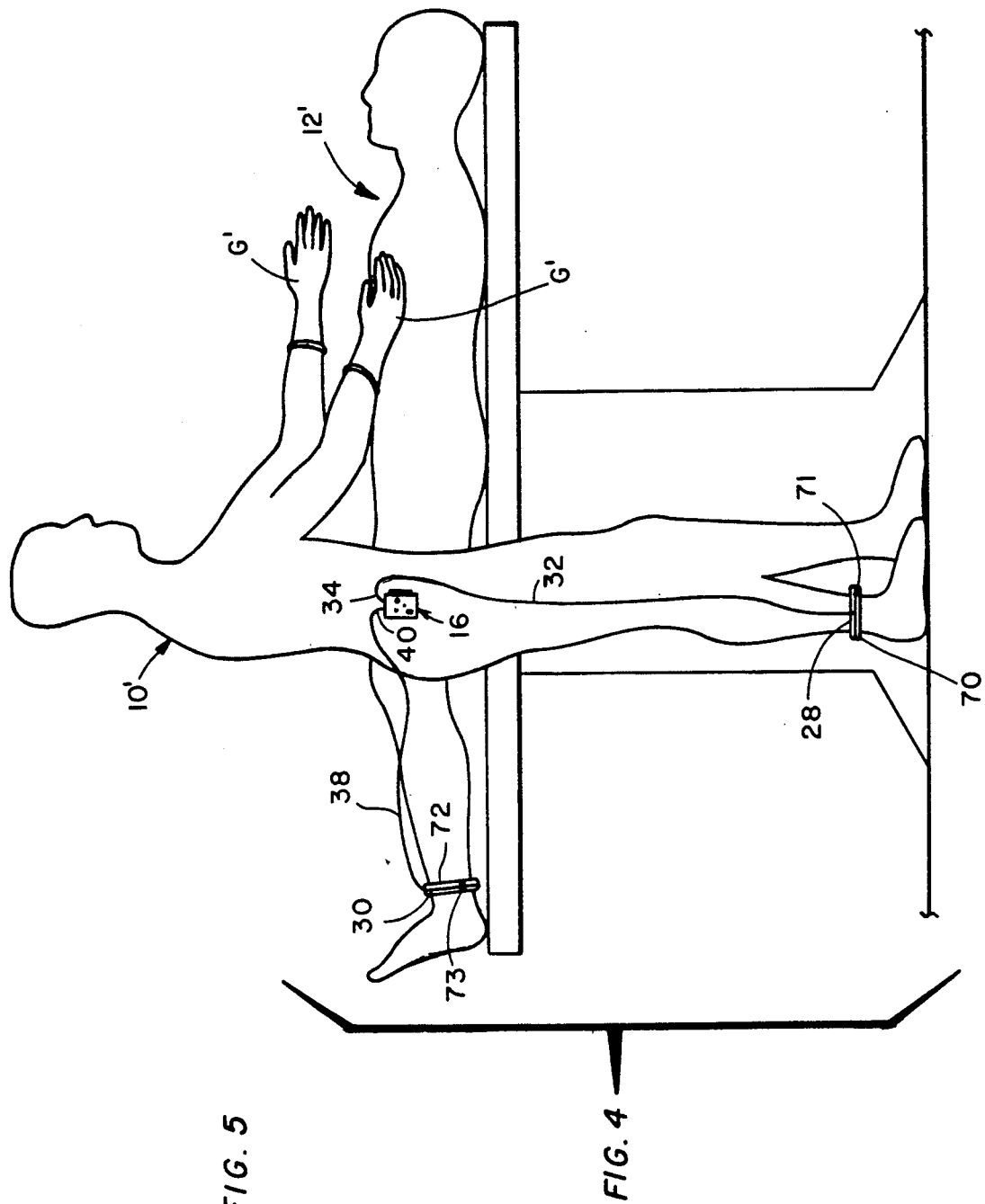
FIG. 4 illustrates a surgical application of the device of the present invention.

A specific application of the device 14 is shown in FIG. 4 wherein a surgeon 10' is performing surgery on a patient 12'. The surgeon is wearing surgical gloves G' and a disposable cuff 70 is attached to his ankle 30' by hook-and-loop fastening element 71 and places contact 28 in electrical contact with the surgeon's body. A second disposable cuff 72 is attached to the patient's ankle by a hook-and-loop fastening means 73 and places contact 36 in electrical contact with the patient's body. The contacts are connected to circuit 44 contained in the portable unit 16 that is shown in FIG. 4 as being worn on the surgeon's belt by fully insulated wires 32 and 38 that are releasably connected to the circuit by jack-like connections 34 and 40 as above discussed.

During surgery, the surgeon is required to place his hands onto and inside of the patient, as shown in FIG. 4, and thus expose his hands to the body and the bodily fluids of the patient. The sensitivity of the circuit is set so that any breach in the surgeon's gloves which is large enough to permit fluid in quantities that are sufficient to endanger the surgeon to contact the surgeon, will complete the circuit and activate the alarm. The inventor has determined that a breach as small as a small pin hole or even as small as one molecule of the workpiece is large enough to permit fluid to penetrate the gloves in quantities sufficient to endanger the surgeon, therefore the sensitivity of the circuit is set so that any fluid from the patient that can flow through a molecule-sized hole in the surgeon's gloves and contact the surgeon's skin will be sufficient to activate the alarm elements. However, other opening sizes can be used if desired, even smaller if suitable. Specifically, in the case of surgery, the opening size can be as small as a single molecule of a patient's body or body fluid, such as a patient's blood, and still be large enough to permit the network to be closed and to actuate the alarm. Of course, any opening larger than this will also cause the alarm to be connected to the power source.

It is also noted that any clothing is suitable as the disclosed protective clothing. The only requirement is that the clothing be capable of preventing electrical contact between the workpiece or any portion of the workpiece and the worker via that clothing when the clothing is in an imperforate condition.

It is understood that while certain forms of the present invention have been illustrated and described herein, it is not to be limited to the specific forms or arrangements of parts described and shown.

I claim:

1. A portable system for continuously monitoring a protective garment for detecting and signalling the occurrence of a breach in such protective garment comprising:
   A) a portable unit which is releasably mounted on a person wearing a protective garment to be monitored, and which includes
      (1) a housing,
      (2) a power source,
      (3) an alarm device,
      (4) a circuit for connecting said alarm device to said power source and which includes
         (a) an amplifier connected to said power source,
         (b) a relay connected to said power source, and
         (c) a sensitivity adjusting element connected to said power source;
   B) normally open switch means for causing said circuit to actuate said alarm device when closed, said switch means being closed when the person's skin contacts some portion of a workpiece on which that person is working, said switch means including
      (1) a first electrical contact element in electrically conducting contact with the person wearing the protective garment being monitored,
      (2) a second electrical contact element in electrically conducting contact with the workpiece,
      (3) a first electrical wire connecting said first electrical contact element with one side of said circuit, said first electrical wire being fully electrically insulated between said first electrical contact element and said circuit,
      (4) a second electrical wire connecting said second electrical contact element with another side of said circuit, said second electrical wire being fully electrically insulated between said second electrical contact element and said circuit,
   said protective garment being electrically insulating and being electrically interposed between said first electrical contact element and said electrically conductive workpiece and preventing formation of an electrically conductive path between said workpiece and said first electrical contact element when said protective garment is imperforate and permitting formation of an electrically conductive path between said workpiece and said first electrical contact element via any perforation in said protective garment, the formation of said electrically conductive path closing said normally open switch and applying power from said power source to said alarm device to activate said alarm device, and
   said sensitivity-adjusting element being set so that any perforation in said protective garment will cause said electrically conductive path to be formed so that the integrity of said protective garment is monitored at all times during any work procedure.

2. The portable system defined in claim 1 wherein said amplifier includes a transistor element.

3. The portable system defined in claim 2 wherein said transistor element includes an NPN transistor.

4. The portable system defined in claim 3 wherein said amplifier has a gain of approximately 25000.

5. The portable system defined in claim 4 wherein said circuit further includes a solenoid-type relay.

6. The portable system defined in claim 5 wherein said sensitivity-adjusting element includes a rheostat-type element.

7. The portable system defined in claim 6 wherein said first electrical contact element includes a disposable cuff element connecting said first electrical contact element to the person wearing the protective garment.

8. The portable system defined in claim 7 wherein said cuff element includes hook-and-loop fastener elements.

9. The portable system defined in claim 8 wherein said cuff element attaches to the person's ankle.

10. The portable system defined in claim 9 wherein said housing further includes a clip element for releasably fastening said housing to the person.

11. The portable system defined in claim 10 wherein said amplifier includes a Darlington pair.

12. The portable system defined in claim 11 wherein said protective garment includes a glove.

13. The portable system defined in claim 11 wherein said protective garment includes a surgical glove.

14. The portable system defined in claim 11 wherein said protective garment includes a boot.

15. The portable system defined in claim 11 wherein said protective garment includes a smock.

16. The portable system defined in claim 11 wherein said protective garment includes a face mask.

17. The portable system defined in claim 11 wherein said protective garment includes pants.

18. The portable system defined in claim 11 wherein said protective garment includes an apron.

19. The portable system defined in claim 11 wherein said workpiece is a fluid container.

20. The portable system defined in claim 19 wherein said fluid container is an animate object.

21. The portable system defined in claim 20 wherein said animate object is a human being.

22. The portable system defined in claim 21 wherein said second electrical contact element is releasably attached to said human being's ankle.

23. The portable system defined in claim 22 wherein said second electrical contact element includes a second cuff element and a hook-and-loop fastener element on said second cuff element.

24. The portable system defined in claim 6 wherein said alarm device includes an audible alarm element.

25. The portable system defined in claim 24 wherein said alarm device includes a visible alarm element.

26. The portable system defined in claim 6 further including first and second jack-like elements on said housing to which said first and second electrical wires are respectively releasably attached.

27. The portable system defined in claim 26 wherein said perforation is greater than approximately one molecule of the workpiece.

* * * * *